United States Patent
Blumhofer et al.

(10) Patent No.: US 11,593,519 B2
(45) Date of Patent: *Feb. 28, 2023

(54) ANONYMISATION OF MEDICAL PATIENT IMAGES USING AN ATLAS

(71) Applicant: Brainlab AG, Munich (DE)

(72) Inventors: Andreas Blumhofer, Neubiberg (DE); Jens Schmaler, Mering (DE)

(73) Assignee: BRAINLAB AG, Munich (DE)

( * ) Notice: Subject to any disclaimer, the term of this patent is extended or adjusted under 35 U.S.C. 154(b) by 105 days.

This patent is subject to a terminal disclaimer.

(21) Appl. No.: 17/225,000

(22) Filed: Apr. 7, 2021

(65) Prior Publication Data

US 2021/0224424 A1    Jul. 22, 2021

Related U.S. Application Data

(63) Continuation of application No. 16/754,419, filed as application No. PCT/EP2019/055052 on Feb. 28, 2019, now Pat. No. 10,977,390.

(51) Int. Cl.
| | |
|---|---|
| *G06K 9/00* | (2022.01) |
| *G06F 21/62* | (2013.01) |
| *G16H 30/40* | (2018.01) |
| *G06T 5/00* | (2006.01) |

(52) U.S. Cl.
CPC .......... *G06F 21/6254* (2013.01); *G06T 5/002* (2013.01); *G16H 30/40* (2018.01)

(58) Field of Classification Search
CPC ...... G06F 21/6254; G16H 30/40; G06T 5/002
See application file for complete search history.

(56) References Cited

U.S. PATENT DOCUMENTS

| | | | | |
|---|---|---|---|---|
| 10,510,449 | B1* | 12/2019 | Reicher | ................ G16H 15/00 |
| 11,436,191 | B2* | 9/2022 | Kuo | ...................... G06F 16/16 |
| 2012/0173283 | A1 | 7/2012 | Kelley | |
| 2016/0224805 | A1 | 8/2016 | Patti | |
| 2017/0372096 | A1 | 12/2017 | Yousfi et al. | |

(Continued)

FOREIGN PATENT DOCUMENTS

| | | |
|---|---|---|
| DE | 102013205482 | 10/2014 |
| EP | 3188058 | 7/2017 |
| EP | 3438869 | 2/2019 |

OTHER PUBLICATIONS

European Intellectual Property Office; International Search Report and Written Opinion of Ser. No. PCT/EP2019/055052; 16 pages; dated Nov. 19, 2019.

*Primary Examiner* — Tom Y Lu
(74) *Attorney, Agent, or Firm* — Gray Ice Higdon

(57) ABSTRACT

Disclosed is a computer-implemented method for generating an anonymized medical image of an anatomical body part of a patient, a corresponding computer program, a program storage medium storing such a program and a computer for executing the program, as well as a medical system comprising an electronic data storage device and the aforementioned computer. The disclosed method encompasses establishing a mapping from a patient image onto an atlas, changing that mapping, and applying the inverse of the changed mapping to the atlas in order to transform image content from the atlas to the patient image in order to achieve a deformed and thereby anonymised appearance of the patient image.

12 Claims, 3 Drawing Sheets

(56) References Cited

U.S. PATENT DOCUMENTS

| | | | |
|---|---|---|---|
| 2018/0068068 A1* | 3/2018 | Bronkalla | G16H 30/40 |
| 2019/0043611 A1 | 2/2019 | Saalbach et al. | |
| 2020/0143084 A1 | 5/2020 | Rosenberg et al. | |
| 2020/0226282 A1* | 7/2020 | Takagi | G16H 30/20 |

* cited by examiner

ANONYMISATION OF MEDICAL PATIENT IMAGES USING AN ATLAS

FIELD OF THE INVENTION

The present invention relates to a computer-implemented method for generating an anonymized medical image of an anatomical body part of a patient, a corresponding computer program, a program storage medium storing such a program and a computer for executing the program, as well as a medical system comprising an electronic data storage device and the aforementioned computer.

TECHNICAL BACKGROUND

It is desirable to anonymize patient faces in medical images in a way that the resulting data set still looks like a real patient data set so that image processing algorithms designed for medical data can still be applied without restrictions to the anonymized scans.

So far face anonymization is done by coarse, non-anatomical modifications of the image in the facial region (e.g. by cutting off the face completely or by strong smoothing of the image in this region to remove biometric details). The result of such modifications looks distinctly different from normal patient images.

Such coarsely modified data sets are no longer representative of real patient scans. Many processing algorithms will not be able to deal with the non-anatomical modifications introduced by the above procedure, since they were optimized to work on normal patient scans (i.e. they might be confused by, for example, a sharp cut plane through the face which is normally oblique in contrast to a normal end plate of a data set). On the other hand, when training machine learning algorithms, such anonymized data will push the algorithm to learn the common, non-anatomical features of the data (e.g. the absence of a face) and such an algorithm would then be unusable on normal data. In the era of machine learning, it is desirable to make the training data as similar as possible to the data on which the algorithm shall later be applied. We thus ideally need original patient data or, if this is not possible for data privacy reasons, well simulated and prepared data.

The present invention has the object of improving anonymization of patient images.

The present invention can be used for anonymising patient image data to make the data suitable for use e.g. on a platform for distribution of medical image data such as Quentry®, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses establishing a mapping from a patient image onto an atlas, changing that mapping, and applying the inverse of the changed mapping to the atlas in order to transform image content from the atlas to the patient image in order to achieve a deformed and thereby anonymised appearance of the patient image.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of generating an anonymized medical image of an anatomical body part of a patient. The method comprises executing, on at least one processor of at least one computer (for example at least one computer being part of an image distribution and/or exchange system and/or platform), the following exemplary steps which are executed by the at least one processor.

In a (for example first) exemplary step, initial patient image data is acquired which describes an initial geometry of the image constituents in a region of the medical image representing the anatomical body part. The medical image is for example two- or three-dimensional image information and has for example been generated by applying a tomographic imaging modality (e.g. computed x-ray tomography, CT, or magnetic resonance tomography, MRI/MRT or ultrasound tomography) or a two-dimensional imaging modality (e.g. radiography) to the anatomical body part. The anatomical body part is an anatomical body part which is suitable for identifying the person of the patient. For example, the anatomical body part includes at least part of the face but in another example alternatively or additionally includes another anatomical body part which is suitable for identifying the person of the patient (for example, the distal phalanx of the thumb). In one example, the anatomical body part comprises soft tissue and at least substantially no bony tissue. For example, the anatomical body part at least substantially comprises only skin tissue and for example additionally soft tissue lying in between the outermost skin surface and bony tissue. This avoids distortion of image information describing bony tissue which, if the disclosed method is used for radiotherapy planning, would severely hamper the usability of the disclosed method for radiotherapy planning because of the strong influence of bony tissue on the propagation of the treatment beam.

In a (for example second) exemplary step, atlas data is acquired which describes an image-based model of the anatomical body part. The atlas data has been generated with the same imaging modality as the initial patient image data or has at least been made comparable to the initial patient image data.

In a (for example third) exemplary step, correspondence mapping data is determined based on the initial patient image data and the atlas data, wherein the initial transformation data describes a positional mapping, called correspondence mapping, between the image constituents in a region of the medical image representing the anatomical body part and an anatomically corresponding part of the image-based model, i.e. a part of the image-based model which corresponds in regard of its anatomical function to the anatomical body part. The correspondence mapping is obtained for example by registering the medical image of the patient to the image-based model, i.e. by executing a registration algorithm on the initial patient image data and the atlas data. In one example, the correspondence mapping is defined to map information described by the initial patient image data onto information described by the atlas data, for example to map the image constituents in a region of the medical image representing the anatomical body part onto an anatomically corresponding body part of the image-based model.

In a (for example fourth) exemplary step, anonymising transformation data is determined based on the correspondence mapping data, wherein the anonymising transformation data describes an anonymising transformation which is determined by altering the correspondence mapping such that the anonymising transformation describes a positional mapping between an image constituent in the region of the medical image defining the anatomical body part and an anatomically non-corresponding part of the image-based model, called non-corresponding body part. For example, the anonymising transformation is determined by smoothing the correspondence mapping. In one more specific example, the smoothing encompasses a smoothing of at least one deformation vector described by the correspondence mapping. In this example of the method according to the first aspect, determining the anonymising transformation encompasses deforming a positional grid (and/or lattice) on which the positions defining the image-based model are defined, and obtaining a deformed image-based model based on the deformed positional grid (and/or lattice). For example, the positional grid and/or lattice on which the positions defining the image-based model in the atlas data is defined is smoothed, for example by changing the angles between grid lines of neighbouring grid cells, for example such that anatomical structures are given a smoother geometry (for example such that discontinuities or surface modulations of at least the corresponding part of the image-based model are at least substantially removed). For example, the smoothing of the at least one deformation vector includes applying a Gaussian filter to the at least one deformation vector described by the correspondence mapping, and the nodes of the grid and/or lattice are re-defined to lie at the tip of the smoothed deformation vector. Alternatively, or additionally, the altering of the correspondence mapping includes setting at least one entry of the at least one deformation vector to a predetermined value, for example zero or an undefined value (e.g. "not-a-number/NaN"). Additionally, the at least one entry is for example given a value which has been obtained based, for example by extrapolation of, of at least one entry of at least one neighbouring unaltered deformation vector which, for example, has not been altered. Alternatively, or additionally, the altering of the correspondence mapping includes adapting the at least one deformation vector to a medical image of another patient or an atlas model of patients of a different type, for example another patient or a cohort of patients of different ethnicity than the patient to whom the anatomical body part belongs. Alternatively, or additionally, the altering of the correspondence mapping includes application of a principal component analysis or a spherical harmonics analysis, of the geometry of corresponding anatomical body parts of patients included in a predetermined population to the image-based model. Thereby, appearance (i.e. the surface geometry) of an anatomical body part including at least part of the face may be changed by adapting it to an "eigen-anatomical body part" such as an "eigenface" of the predetermined population which is defined by the eigenmodes of the principal component analysis of the surface geometry of the corresponding anatomical body parts. In one example, the coefficients of the principal components analysis or spherical harmonics analysis, respectively, have been or are randomised in order to achieve a higher degree of anonymization. Notably, even if the correspondence mapping is changed for generation of the anonymization transformation, the image-based model described by the atlas data remains unchanged concerning the image information which is only moved to a different position in a global coordinate system in dependence on the change to the grid and/or lattice defining position in the image-based model. This results in that the correspondence mapping is configured to map image content in the medical image onto corresponding image content of the image-based model, whereas the anonymization transformation is configured to map a position in the grid and/or lattice (for example, the smoothed grid and/or lattice) defining the positions of the image-based model onto the same position in a grid and/or lattice defining the positions in the medical image. In other words, the image-based model is not deformed by the alteration to the correspondence mapping. Rather, the corresponding part is moved to a different position in the coordinate system defined by the grid/lattice of the atlas. Its previous position is, due to deforming the lattice/grid of the atlas, assigned to the non-corresponding part of the image-based model which does not anatomically corresponds to the anatomy present at the same position in the grid/and or lattice defining positions in the medical image.

In a (for example fifth) exemplary step, anonymised patient image data is determined based on the initial patient image data and the atlas data and the correspondence mapping data and the anonymising transformation data, wherein the anonymised patient image data describes an image representation of the non-corresponding body part at the position of at least one of the image constituents in the region of the medical image representing the anatomical body part. For example, the correspondence mapping is invertible and the anonymised patient image data is determined by applying the inverse of the altered correspondence mapping to the part of the image-based model defining the non-corresponding body part, i.e. by mapping information described by the atlas data onto information described by the initial patient image data. Thereby, the part of the image-based model defining the non-corresponding body part is registered with the image constituents in the region of the medical representing the anatomical body part. For example, the inverse of the correspondence mapping is applied to the non-corresponding body part in order to map it onto a certain position in the medical image (i.e. in the grid defining the medical image) described by the initial patient image data so as to determine the anonymised patient image data which describes the anonymized patient image.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method, for example the steps of the method, according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a computer-readable program storage medium on which the program according to the second aspect is stored. The program storage medium is for example non-transitory.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
the at least one computer according to the fourth aspect; and
at least one electronic data storage device storing at least the initial patient image data,
wherein the at least one computer is operably coupled to
the at least one electronic data storage device for acquiring, from the at least one data storage device, at least the initial patient image data and the atlas data.

In a sixth aspect, the present invention also relates to the use of the system according to the fifth aspect for exchanging the anonymised patient image data for example between medical entities such as users or institutions. The use comprises execution of the steps of the method according to any one of the preceding method claims for preparing the exchange.

For example, the invention does not involve or in particular comprise or encompass an invasive step which would represent a substantial physical interference with the body requiring professional medical expertise to be carried out and entailing a substantial health risk even when carried out with the required professional care and expertise. For example in the sixth aspect, the invention relates only to exchanging data usable in a medical procedure rather than actually executing a medical procedure.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

The movements of the treatment body parts are for example due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. For example, analytical devices are constituted to perform medical imaging methods. Analytical devices for example use medical imaging methods and are for example devices for analysing a patient's body, for instance by using waves and/or radiation and/or energy beams, for example electro-magnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analysing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part. Tracking an indicator body part thus allows a movement of the treatment body part to be tracked on the basis of a known correlation between the changes in the position (for example the movements) of the indicator body part and the changes in the position (for example the movements) of the treatment body part. As an alternative to or in addition to tracking indicator body parts, marker devices (which can be used as an indicator and thus referred to as "marker indicators") can be tracked using marker detection devices. The position of the marker indicators has a known (predetermined) correlation with (for example, a fixed relative position relative to) the position of indicator structures (such as the thoracic wall, for example true ribs or false ribs, or the diaphragm or intestinal walls, etc.) which for example change their position due to vital movements.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: www.elekta.com/healthcare_us_elekta_vmat.php and www.varian.com/us/oncology/treatments/treatment_techniques/rapidarc.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. Image fusion is for example used for registering one dataset to another datasets, wherein the datasets for example comprise image information or for example have been generated on the basis of image information. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
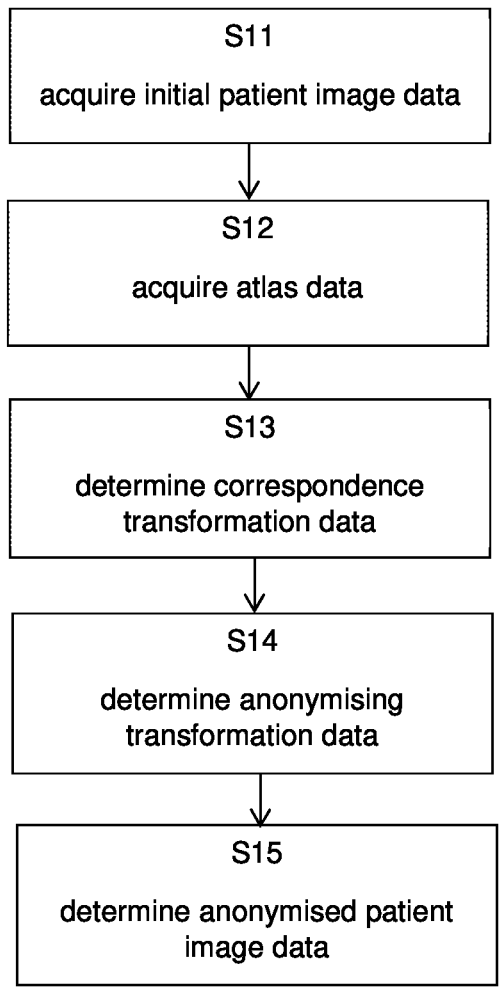
FIG. 1 illustrates the basic flow of the method according to the first aspect.

FIG. 1 illustrates the basic steps of the method according to the first aspect, in which step S11 encompasses acquisition of the initial patient image data, followed by step S12 which encompasses acquisition of the atlas data. Subsequent step S13 encompasses determination of the correspondence mapping data, which serves as a basis for determining in step S14 the anonymising transformation data. On the basis of the data determined and acquired in the foregoing steps, the anonymised patient image data is then determined in step S15.

Figure 2A:
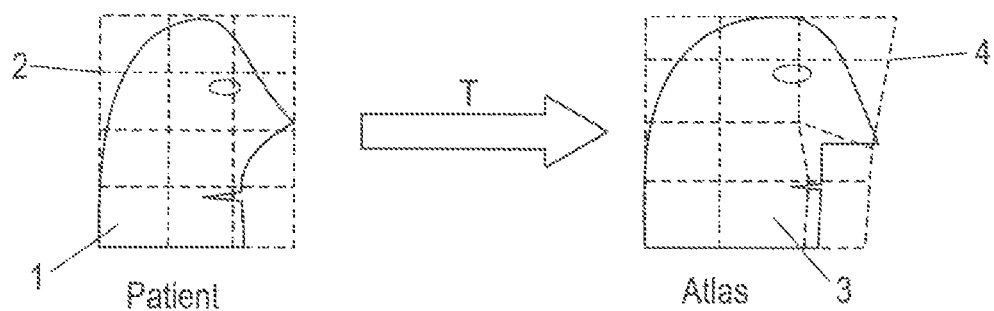
FIGS. 2a to 2c illustrate the chain of transformation encompassed by the method according to the first aspect.

FIG. 2a describes the correspondence mapping T from a patient image showing a patient's head 1 onto an atlas showing an image-based model 3 of the head. The positions in the patient image are defined on a grid 2, and the positions in the atlas are defined in a grid 4.

Figure 2B:
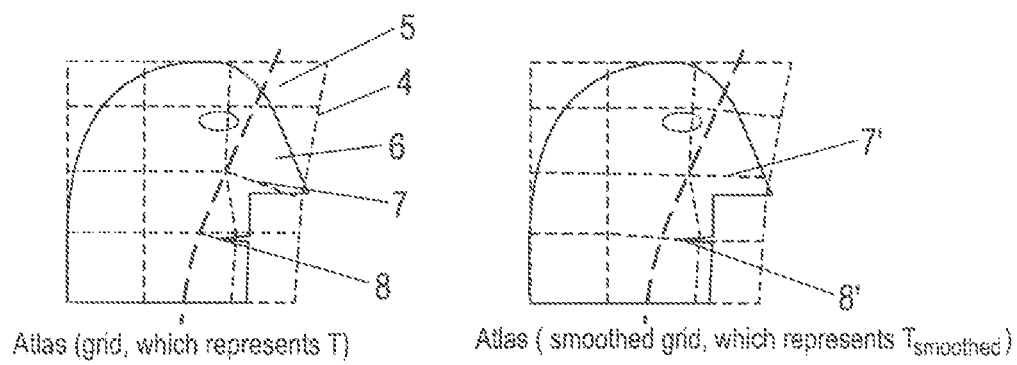
Figure 2C:
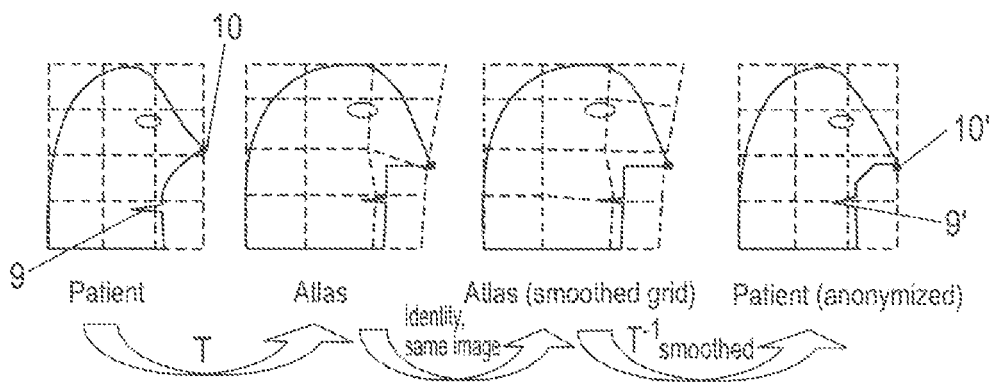

FIG. 2b shows how an area 5 (delineated by a dashed line) in the image-based model 3 which shall serve as a region available for anonymising the medical image showing the patient is smoothed by changing the orientation of grid lines 7, 8 to that of grid lines 7', 8', thereby obtaining a smoothed version of T which is denoted as $T_{smoothed}$. The left half of FIG. 2b shows the unchanged state of the grid defining the positions in the image-based model, and the right half of FIG. 2b shows its changed state. Notably, the image-based model 3 is not deformed by smoothing the grid. The constituents of the image-based model 4 are assigned to different positions on the grid, though, compared to the right half of FIG. 2b. FIG. 2c illustrates the chain of transformations executed for anonymising the initial patient image by application of the method according to the first aspect. The initial patient image data includes a medical image of the tip of the patient's nose 10 and of the patient's open mouth 9 which are to be used as the anatomical body part the representation of which shall be anonymised. First, the correspondence mapping from the initial patient data to the atlas data is established and then altered by smoothing the grid defining the positions in the image-based model 3 to determine the anonymising transformation, which is equal to the inverse of the altered (smoothed) correspondence mapping $T_{smoothed}^{-1}$. This anonymising transformation is then applied to the correspondence part in the image-based model (indicated a black spot on the tip of the nose). The result is a medical image of the patient in which the shape of the facial region around nose 10' and mouth 9' is changed relative to the initial patient image data.

Figure 3:
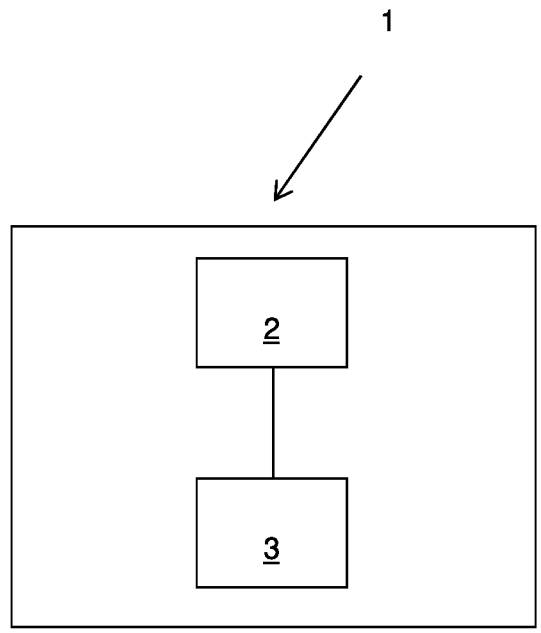
FIG. 3 is a schematic illustration of the system according to the fifth aspect.

FIG. 3 is a schematic illustration of the medical system 1 according to the fifth aspect. The system is in its entirety identified by reference sign 1 and comprises a computer 2, an electronic data storage device (such as a hard disc) 3 for storing at least the initial patient image data and the atlas data. The components of the medical system 1 have the functionalities and properties explained above with regard to the fifth aspect of this disclosure.

An alternative short description of the disclosed invention is given in the following.

The target of the procedure is to establish a real face anonymization for volumetric medical scans of human patients, such as the three-dimensional image volumes acquired by MRI and CT scanners. The procedure is as follows:

The original data set is a for example three-dimensional image volume depicting human anatomy, possibly including the facial region.

Start from an original data set (we can also start from an already anonymized data set).

Determine the registration of the data set to an atlas.

If the data set is an original data set, destroy the registration mapping in the regions which have to be anonymized. This can be the whole face including bones, only the facial skin or maybe only the nose or chin. The region of interest for anonymization is first transformed from the atlas to the patient data set. In this region, the deformation vectors pointing from the patient into the atlas are then reset to "not set".

The destroyed mapping parts must afterwards be reconstructed by one of the following methods:

By just doing a mathematical continuation of the deformation vectors (i.e. the "not set" vectors are reconstructed from the remaining vectors by some kind of extrapolation). This will let the patient look a little more like the atlas (but still anatomically plausible). The larger the regions in which the original deformation has been removed, the larger the difference between original and anonymized patient scan. If the anonymization region is chosen too small, the difference may be insufficient and the extrapolation may reconstruct sufficient biometric details to allow for patient identification (similar to what is done in forensic face reconstruction).

By continuation plus additional (specifically chosen) reproducible or random deformations within an anatomically plausible range, such as making the nose longer or shorter, making the chin higher or lower, making the cheeks thinner or thicker, changing to Asiatic style.

By using principal modes, the anatomical body part such as the human face (similar to shape models). These modes can be combined with random coefficients in a suitable range to generate a new artificial (but anatomically plausible) face. Depending on which tissue should be preserved, all modes or only the higher order modes are used to transform the face to a totally different but real looking individuum.

The invention claimed is:

1. A computer-implemented method for generating an anonymized medical image of a patient, the method comprising:

acquiring initial patient image data which describes an initial geometry of image constituents of the anonymized medical image representing an anatomical body part;

acquiring atlas data which describes an image-based model of the anatomical body part having a part which anatomically corresponds and a part which does not anatomically correspond to the anatomical body part of the patient;

determining correspondence mapping data based on the initial patient image data and the atlas data, wherein the correspondence mapping data describes a positional mapping between the image constituents of the anonymized medical image and the anatomically corresponding part of the image-based model;

determining anonymising transformation data based on the correspondence mapping data, by altering the positional mapping, describing the positional mapping between an image constituent of the anonymized medical image and the anatomically non-corresponding part of the image-based model;

determining anonymised patient image data based on at least the anonymising transformation data describing an image representation of the anatomically non-corresponding part of the image-based model at the position of at least one of the image constituents in the anonymized medical image.

2. The method of claim 1 wherein the correspondence mapping data is invertible.

3. The method of claim 2 wherein the anonymised patient image data is determined applying the inverse of the altered positional mapping to the part of the image-based model defining the anatomically non-corresponding part of the image-based model to determine the anonymised patient image data.

4. The method according to claim 1, wherein the anonymising transformation data is determined by smoothing the positional mapping.

5. The method according to claim 4, wherein the smoothing encompasses a smoothing of at least one deformation vector described by the positional mapping.

6. The method according to claim 5, wherein the smoothing of the at least one deformation vector includes applying a Gaussian filter to the at least one deformation vector.

7. The method according to claim 5, wherein the altering the positional mapping includes setting at least one entry of the at least one deformation vector to a predetermined value.

8. The method according to claim 7, wherein the at least one entry is given a value which has been obtained based on at least one entry of at least one neighbouring unaltered deformation vector.

9. The method according to claim 5, wherein the altering of the positional mapping includes adapting the at least one deformation vector to a medical image of another patient.

10. The method according to claim 1, wherein the altering of the positional mapping includes application of a principal component analysis or a spherical harmonics analysis of the geometry of corresponding anatomical body parts of patients included in a predetermined population to the image-based model.

11. The method according to claim 1, wherein determining the anonymising transformation data further comprises:

deforming a positional grid on which the positions defining the image-based model are defined, and obtaining a deformed image-based model based on the deformed positional grid.

12. A computer-implemented method for generating an anonymized medical image of a patient, the method comprising:

acquiring initial patient image data having image constituents of the anonymized medical image representing an anatomical body part;

acquiring atlas data representing an image-based model of the anatomical body part having a part which anatomically corresponds and a part which does not anatomically correspond to the anatomical body part of the patient;

determining correspondence mapping data based on the initial patient image data and the atlas data, the correspondence mapping data describing a positional mapping between the image constituents of the anonymized medical image and the anatomically corresponding part of the image-based model;

determining anonymising transformation data based on the correspondence mapping data, the anonymising transformation data describing the positional mapping between an image constituent of the anonymized medical image and the anatomically non-corresponding part of the image-based model;

determining anonymised patient image data based on at least the anonymising transformation data, wherein the anonymised patient image data describes an image representation of the anatomically non-corresponding part of the image-based model at the position of at least one of the image constituents in the anonymized medical image.

* * * * *